(12) United States Patent
Viola

(10) Patent No.: US 8,308,044 B2
(45) Date of Patent: Nov. 13, 2012

(54) FLEXIBLE ENDOLUMINAL SURGICAL INSTRUMENT

(75) Inventor: Frank J. Viola, Sandy Hook, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 231 days.

(21) Appl. No.: 12/761,562

(22) Filed: Apr. 16, 2010

(65) Prior Publication Data
US 2010/0200640 A1    Aug. 12, 2010

Related U.S. Application Data

(63) Continuation of application No. 11/787,989, filed on Apr. 17, 2007, now Pat. No. 7,708,182.

(51) Int. Cl.
*A61B 17/068* (2006.01)
*A61B 17/072* (2006.01)

(52) U.S. Cl. ............... 227/178.1; 227/175.1; 227/179.1

(58) Field of Classification Search ............ 227/175.1, 227/176.1, 178.1, 179.1; 606/1, 139; 74/500.5, 74/501.6, 502.6
See application file for complete search history.

(56) References Cited

U.S. PATENT DOCUMENTS

| | | |
|---|---|---|
| 3,079,606 A | 3/1963 | Bobrov et al. |
| 3,490,675 A | 1/1970 | Green et al. |
| 3,638,652 A | 2/1972 | Kelley |
| 4,331,277 A | 5/1982 | Green |
| 4,349,028 A | 9/1982 | Green |
| 4,473,077 A | 9/1984 | Noiles et al. |
| 4,485,817 A | 12/1984 | Swiggett |
| 4,488,523 A | 12/1984 | Shichman |
| 4,499,895 A | 2/1985 | Takayama |
| 4,576,167 A | 3/1986 | Noiles |
| 4,589,412 A | 5/1986 | Kensey |
| 4,688,555 A | 8/1987 | Wardle |
| 4,941,466 A | 7/1990 | Romano |
| 4,991,763 A | 2/1991 | Storace |
| 5,005,749 A | 4/1991 | Aranyi |
| 5,114,065 A | 5/1992 | Storace |
| 5,119,983 A | 6/1992 | Green et al. |
| 5,207,691 A | 5/1993 | Nardella |
| 5,219,111 A | 6/1993 | Bilotti et al. |
| 5,258,007 A | 11/1993 | Spetzler et al. |
| 5,258,008 A | 11/1993 | Wilk |
| 5,271,543 A | 12/1993 | Grant et al. |
| 5,271,544 A | 12/1993 | Fox et al. |
| 5,275,322 A | 1/1994 | Brinkertoff et al. |
| 5,285,945 A | 2/1994 | Brinkertoff et al. |
| 5,292,053 A | 3/1994 | Bilotti et al. |
| 5,292,326 A | 3/1994 | Green et al. |

(Continued)

OTHER PUBLICATIONS

European Search Report for EP 08251443.1-2310 date of completion is Mar. 19, 2010 (3 pages).

*Primary Examiner* — Hemant M Desai
*Assistant Examiner* — Gloria R Weeks

(57) ABSTRACT

A surgical instrument comprises a first elongated member and a second elongated member, the first elongated member and the second elongated member being operatively connected and configured to rotate in opposite directions to substantially limit counter torque. The first and second elongated members are flexible shafts. The surgical instrument can be configured to apply fasteners to a tissue portion. This embodiment of the surgical instrument includes a cartridge having a plurality of fasteners, an anvil, said anvil and cartridge being relatively movable between spaced and approximated positions, and a sled disposed in the cartridge. The sled includes a cam member. The cam member is designed to drive the fasteners through tissue and toward the anvil.

19 Claims, 18 Drawing Sheets

U.S. PATENT DOCUMENTS

| | | | | |
|---|---|---|---|---|
| 5,336,229 | A * | 8/1994 | Noda | 606/144 |
| 5,348,259 | A | 9/1994 | Blanco et al. | |
| 5,433,721 | A | 7/1995 | Hooven et al. | |
| 5,452,836 | A | 9/1995 | Huitema et al. | |
| 5,465,894 | A | 11/1995 | Clark et al. | |
| 5,482,197 | A | 1/1996 | Green et al. | |
| 5,509,918 | A | 4/1996 | Romano | |
| 5,564,615 | A | 10/1996 | Bishop et al. | |
| 5,580,067 | A | 12/1996 | Hamblin et al. | |
| 5,588,580 | A | 12/1996 | Paul et al. | |
| 5,588,581 | A | 12/1996 | Conlon et al. | |
| 5,601,224 | A | 2/1997 | Bishop et al. | |
| 5,626,587 | A | 5/1997 | Bishop et al. | |
| 5,634,584 | A | 6/1997 | Okorocha et al. | |
| 5,662,662 | A | 9/1997 | Bishop et al. | |
| 5,676,674 | A | 10/1997 | Bolanos et al. | |
| 5,732,871 | A | 3/1998 | Clark et al. | |
| 5,779,130 | A | 7/1998 | Alesi et al. | |
| 5,865,361 | A | 2/1999 | Milliman et al. | |
| 5,868,760 | A | 2/1999 | McGuckin, Jr. | |
| 5,915,616 | A | 6/1999 | Viola et al. | |
| 5,954,259 | A * | 9/1999 | Viola et al. | 227/176.1 |
| 5,964,394 | A | 10/1999 | Robertson | |
| 6,119,913 | A | 9/2000 | Adams et al. | |
| 6,126,058 | A | 10/2000 | Adams et al. | |
| 6,193,129 | B1 | 2/2001 | Bittner et al. | |
| 6,202,914 | B1 | 3/2001 | Geiste et al. | |
| 6,241,139 | B1 | 6/2001 | Milliman et al. | |
| 6,264,087 | B1 | 7/2001 | Whitman | |
| 6,505,768 | B2 | 1/2003 | Whitman | |
| 6,520,971 | B1 | 2/2003 | Perry et al. | |
| 6,530,932 | B1 * | 3/2003 | Swayze et al. | 606/144 |
| 6,698,643 | B2 | 3/2004 | Whitman | |
| 6,743,240 | B2 | 6/2004 | Smith et al. | |
| 6,824,548 | B2 | 11/2004 | Smith et al. | |
| 6,843,403 | B2 | 1/2005 | Whitman | |
| 7,114,642 | B2 | 10/2006 | Whitman | |
| 7,556,185 | B2 | 7/2009 | Viola | |
| 7,721,930 | B2 * | 5/2010 | McKenna et al. | 227/176.1 |
| 7,909,221 | B2 * | 3/2011 | Viola et al. | 227/175.1 |
| 8,038,044 | B2 * | 10/2011 | Viola | 227/175.1 |
| 8,181,840 | B2 * | 5/2012 | Milliman | 227/179.1 |
| 2003/0130677 | A1 | 7/2003 | Whitman | |
| 2003/0132268 | A1 | 7/2003 | Whitman | |
| 2005/0049616 | A1 | 3/2005 | Rivera et al. | |
| 2005/0125010 | A1 | 6/2005 | Smith et al. | |
| 2005/0205640 | A1 * | 9/2005 | Milliman | 227/176.1 |
| 2007/0023477 | A1 | 2/2007 | Whitman et al. | |
| 2007/0088343 | A1 | 4/2007 | McIntyre et al. | |
| 2009/0090764 | A1 | 4/2009 | Viola | |
| 2009/0236399 | A1 | 9/2009 | Bilotti | |
| 2011/0139852 | A1 * | 6/2011 | Zingman | 227/176.1 |

* cited by examiner

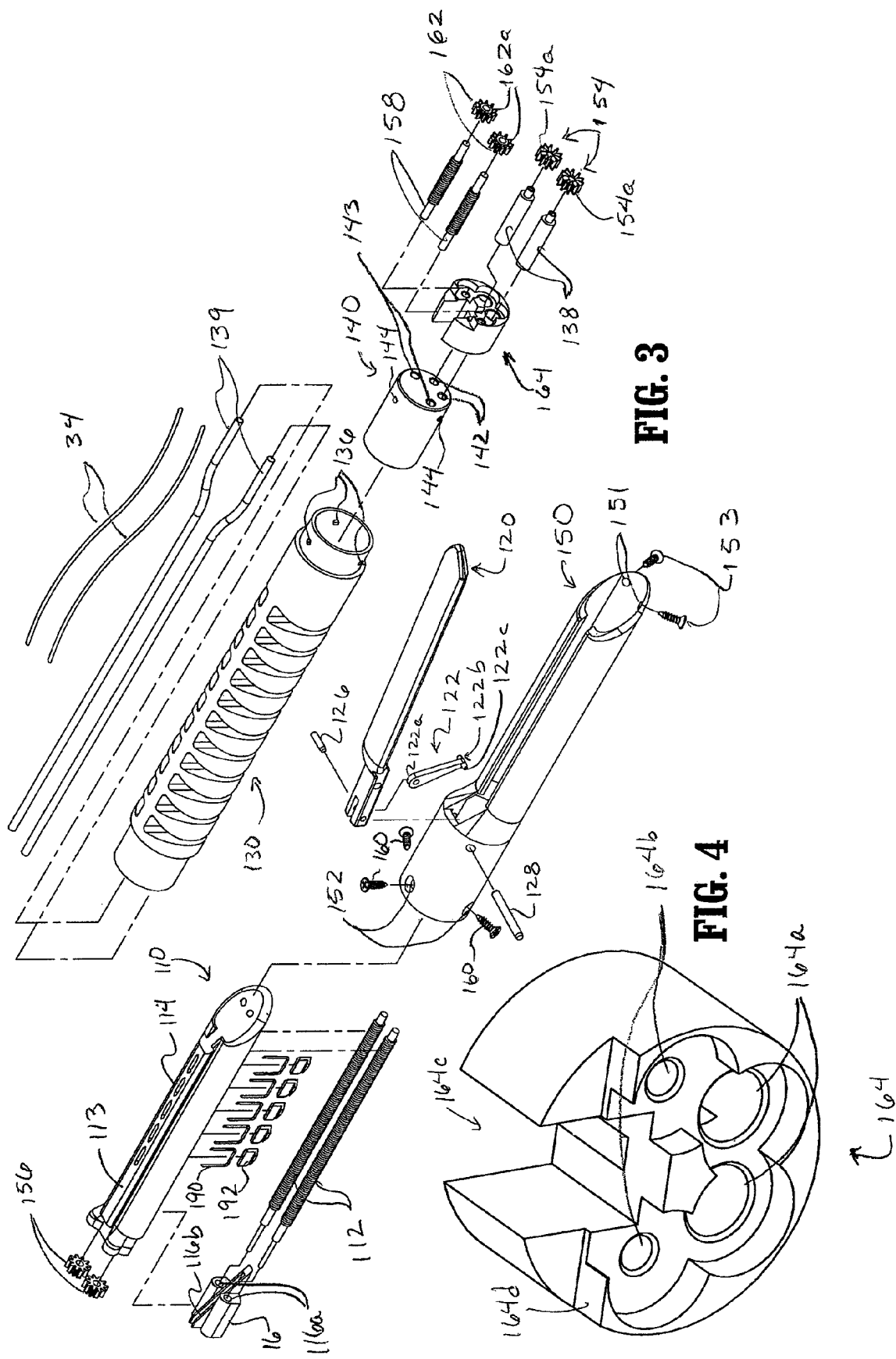

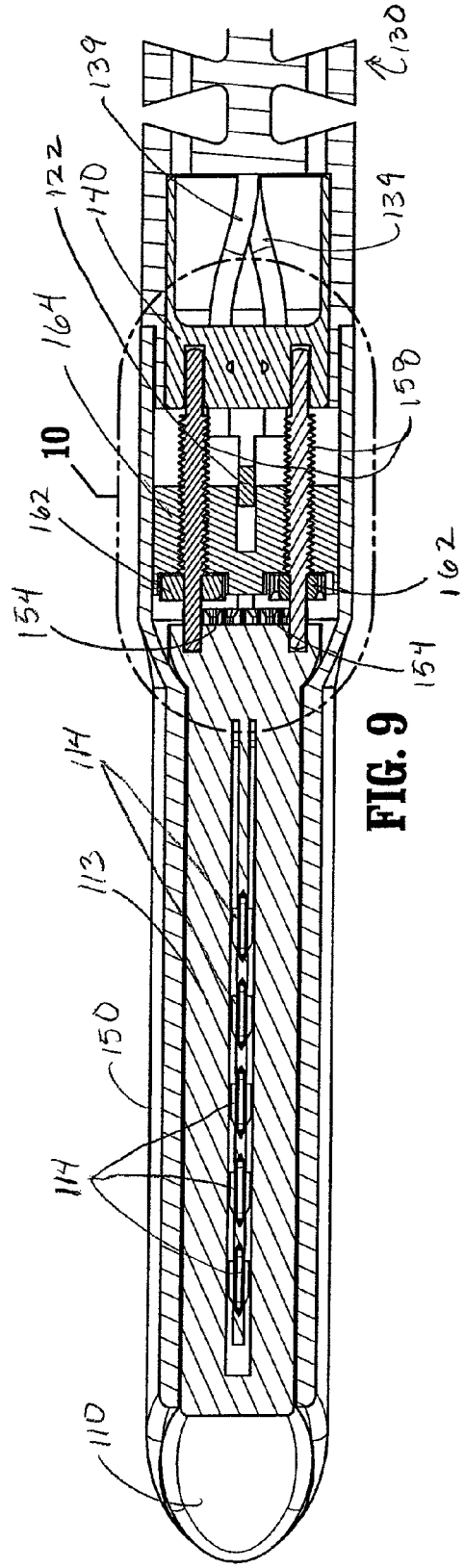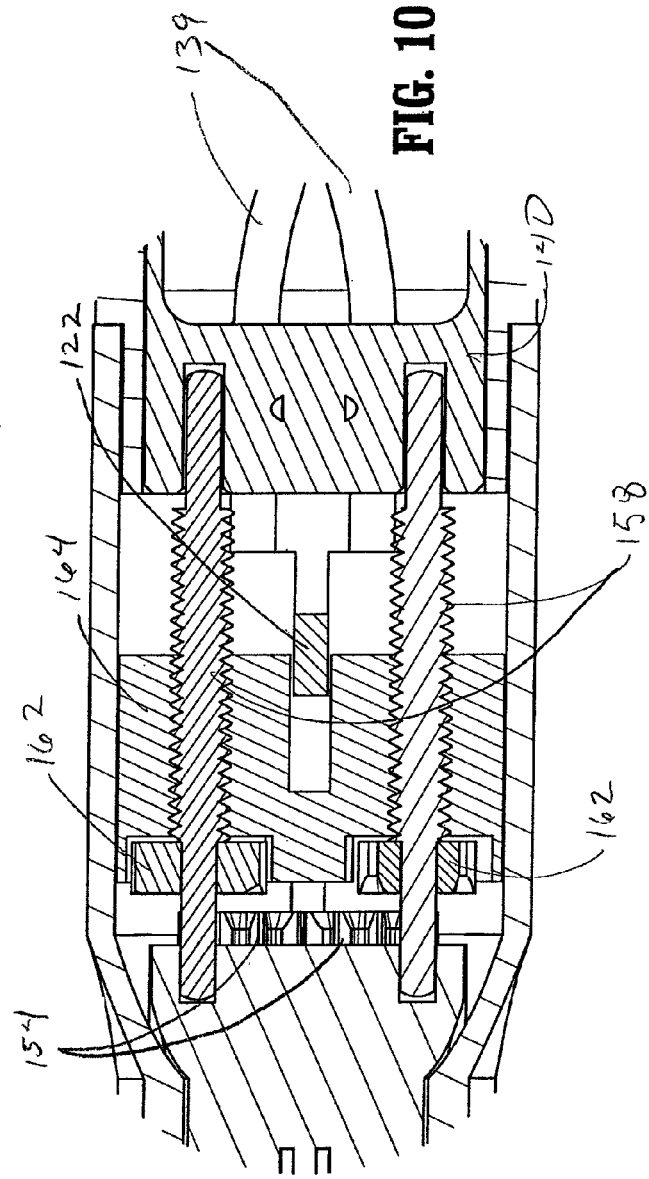

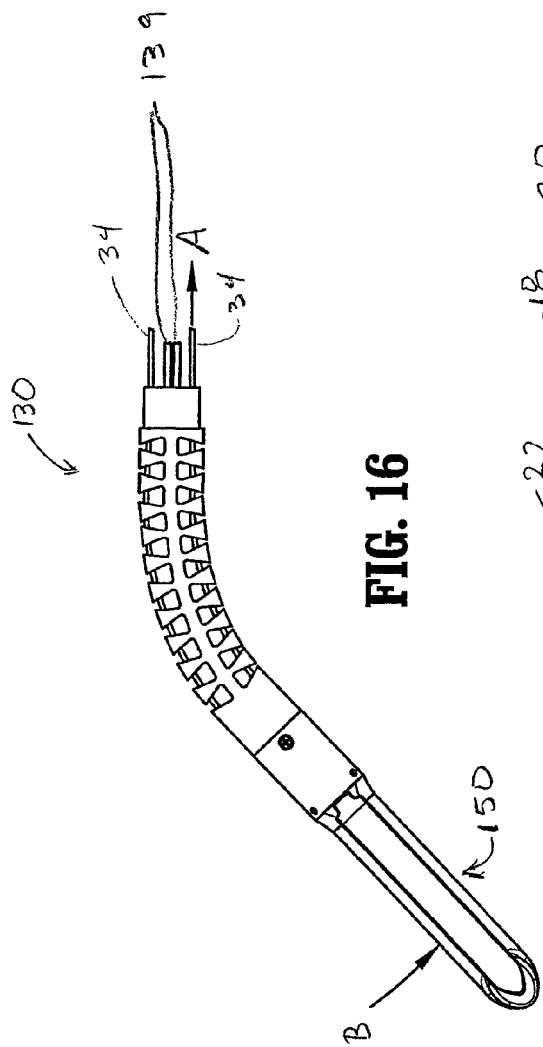
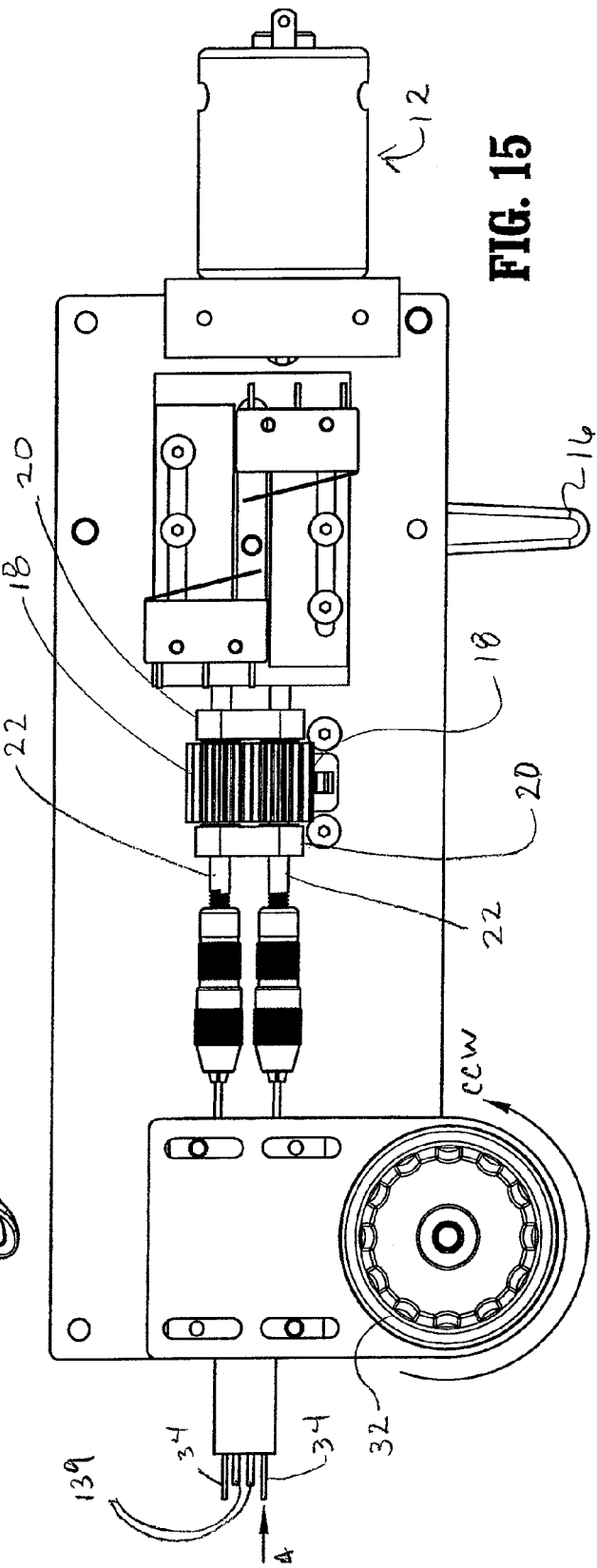

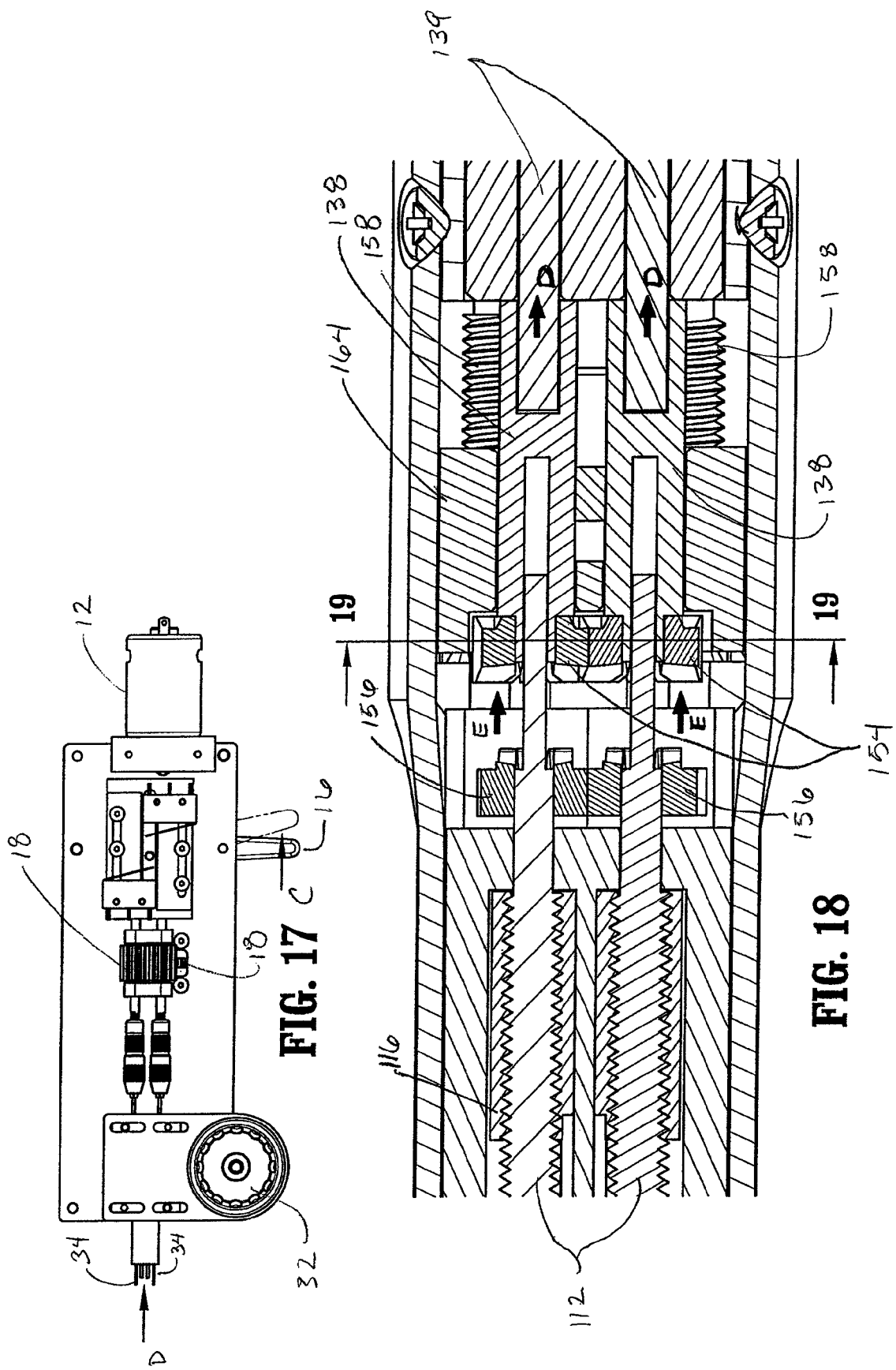

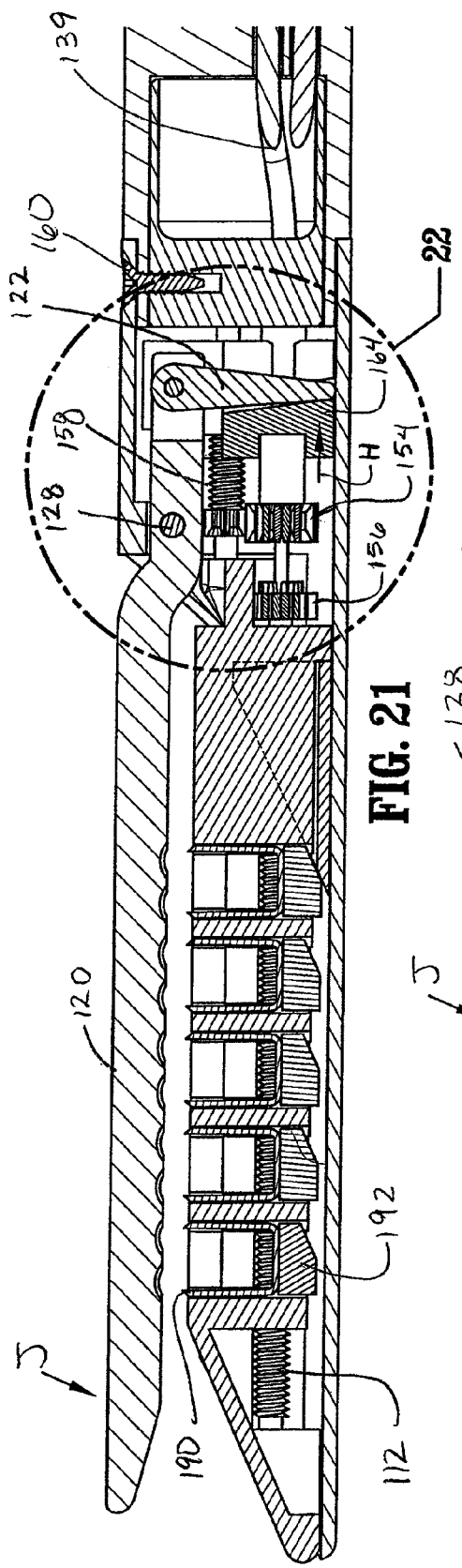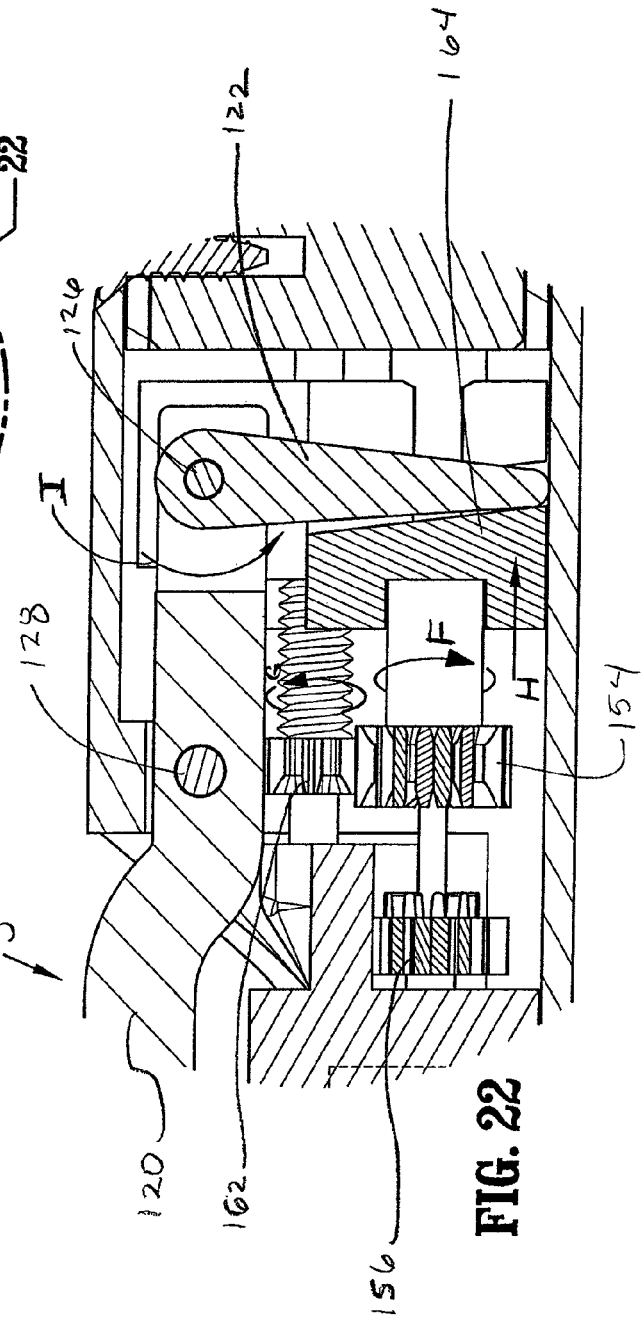

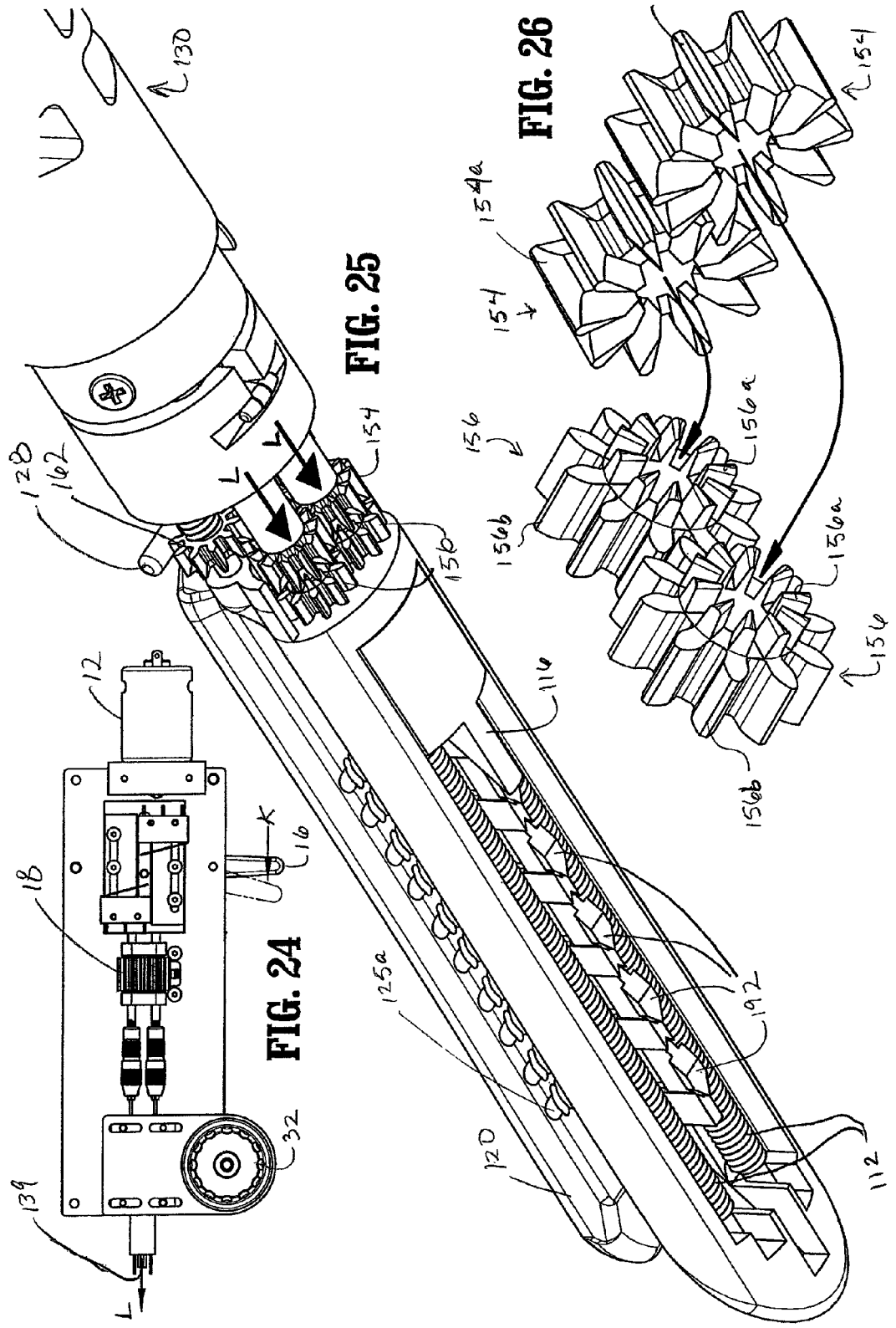

FLEXIBLE ENDOLUMINAL SURGICAL INSTRUMENT

CROSS-REFERENCE TO RELATED APPLICATIONS

This application is a continuation of U.S. application Ser. No. 11/787,989 filed Apr. 17, 2007, now U.S. Pat. No. 7,708,182, and the disclosures of each of the above-identified applications are hereby incorporated by reference in their entirety.

BACKGROUND

1. Technical Field

The present disclosure relates to an apparatus and method for surgical devices. More particularly, the present disclosure relates to a surgical instrument capable of eliminating or substantially limiting counter torque in a surgical fastening apparatus.

2. Background of Related Art

Surgical fastening devices wherein tissue is first grasped or clamped between opposing jaw structure and then joined by surgical fasteners are well known in the art. Several types of known surgical fastening instruments are specifically adapted for use in various procedures such as end-to-end anastomosis, gastrointestinal anastomosis, endoscopic gastrointestinal anastomosis, and transverse anastomosis among others. U.S. Pat. Nos. 5,915,616; 6,202,914; 5,865,361; and 5,964,394 are examples of surgical fastening instruments. Although the fasteners are typically in the form of surgical staples, two-part polymeric fasteners may also be employed.

Surgical fastening instruments can include two elongated jaw members used to capture or clamp tissue. One jaw member typically contains a staple cartridge that houses a plurality of staples arranged in a single row or a plurality of rows while the other jaw member has an anvil that defines a surface for forming the staple legs as the staples are driven from the staple cartridge. The stapling operation is usually effected by one or more cam members that translate through the staple cartridge, with the cam members acting upon staple pushers to sequentially or simultaneously eject the staples from the staple cartridge. A knife may be provided to move axially between the staple rows to cut or open the stapled tissue between the rows of staples. U.S. Pat. Nos. 3,079,606 and 3,490,675 disclose examples of this kind of instrument.

Some surgical fastening instruments contain rotating components that facilitate actuation of the surgical instrument, deployment of the surgical fasteners, or articulation of the surgical instrument. For instance, U.S. Pat. No. 7,114,642 to Whitman ("Whitman") discloses a stapling mechanism including two rotating flexible drive shafts. One drive shaft controls the movement of an upper jaw while the other drive shaft controls the stapling and cutting actions of the mechanism. Essentially, the flexible drive shafts transmit torque from a motor in a handle to the distal end of the shaft. Each drive shaft is driven by a different motor and they are not operatively connected with each other. The torque transmitted by each drive shaft produces a counter torque that can turn or steer the jaws of the surgical mechanism to one direction. This undesirable motion of the jaws can prevent the surgeon from having full control of the surgical instrument. The stapling mechanism of Whitman does not have any mechanism, device, or component to eliminate the detrimental effects of the torque, i.e., the counter torque. Other surgical instruments having torque transmitting components also fail to provide adequate measures to limit or eliminate counter torque. Therefore, it is desirable to develop a surgical instrument capable of eliminating or substantially limiting counter torque.

SUMMARY

The presently disclosed a surgical instrument includes a first elongated member and a second elongated member. The first elongated member and the second elongated member are operatively connected to each other and configured to rotate in opposite directions to substantially limit counter torque. These elongated members can consist of flexible shafts. Because the shafts are operatively connected to one another, they are redundant and can fully operate the instrument even if one of the shafts breaks.

An embodiment of the surgical instrument includes a cartridge housing a plurality of fasteners, an anvil, a sled disposed in the cartridge, and first and second elongated members disposed in the cartridge. The anvil and the cartridge are relatively movable between spaced and approximated positions. The cartridge has a sled positioned therein. The sled includes a cam member designed to drive the fasteners through tissue and toward the anvil, and at least one bore disposed therethrough for receiving at least one drive member. One or more drive members can be operatively attached to the first or second elongated members, or both. The drive member can optionally consist of a lead screw. The surgical instrument further includes a channel partially encompassing the cartridge and a neck. The neck, which is flexible, is secured to the channel.

BRIEF DESCRIPTION OF THE DRAWINGS

Embodiments of the presently disclosed surgical instrument are described herein with reference to the accompanying drawings, wherein:

FIG. 3 is a perspective exploded view of the surgical instrument of FIGS. 1 and 2;

FIG. 4 is an perspective view of a clamp cam of the surgical instrument of FIGS. 1-3;

FIG. 9 is a top cross-sectional view of the surgical instrument of FIGS. 1-3;

FIG. 10 is a top sectional view of the surgical instrument of FIGS. 1-3, taken around section 10 of FIG. 9;

FIG. 15 is a top view of the actuation apparatus of FIG. 1;

FIG. 16 is a top view of the surgical instrument of FIGS. 1-3;

FIG. 17 is a top view of the actuation apparatus of FIGS. 1 and 15;

FIG. 18 is a top cross-sectional view of a portion of the surgical instrument of FIGS. 1-3;

FIG. 21 is a side cross-sectional view of a portion of the surgical instrument of FIGS. 1-3;

FIG. 22 is a side sectional view of a portion of the surgical instrument of FIGS. 1-3, as taken around section 22 of FIG. 21;

FIG. 24 is a top view of the actuation apparatus of FIGS. 1, 15 and 17;

FIG. 25 is a perspective view of a portion of the surgical instrument of FIGS. 1-3;

FIG. 26 is a perspective view of the gear couplers and pinions of a surgical instrument in accordance with an embodiment of the present disclosure;

DETAILED DESCRIPTION OF THE EMBODIMENTS

Figure 1:
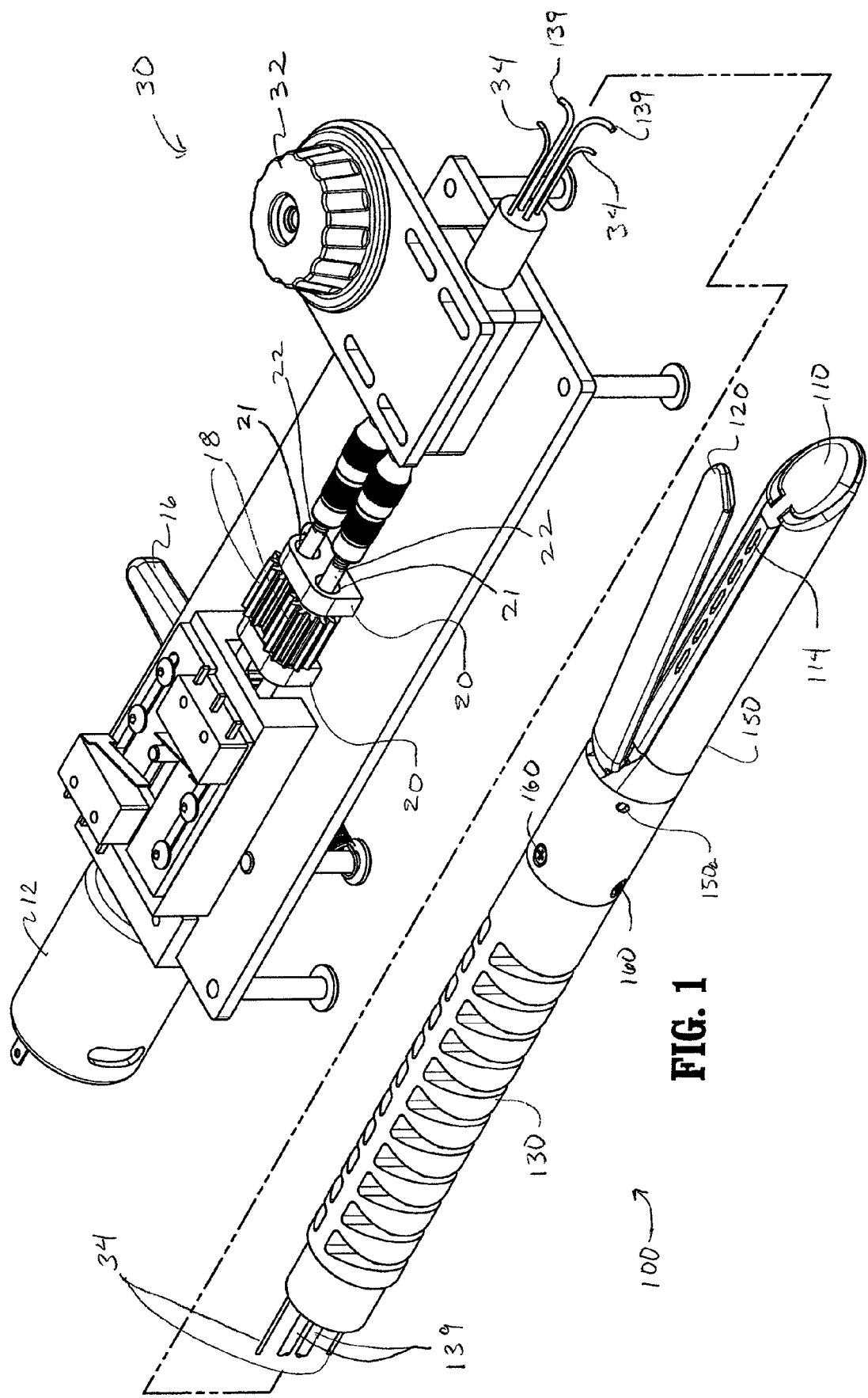
FIG. 1 is a perspective view of a surgical instrument in accordance with an embodiment of the present disclosure operatively connected to an actuation apparatus.

Embodiments of the presently disclosed surgical instrument will now be described in detail with reference to the drawings wherein like reference numerals identify similar or identical elements. In the drawings and in the description which follows, the term "proximal," as is traditional, will refer to the end of the surgical instrument that is closest to the operator while the term "distal" will refer to the end of the surgical instrument that is farthest from the operator. In the present disclosure, the words "a," "an," or "the" are to be taken to include both the singular and the plural. Likewise, any reference to plural items shall, where appropriate, include the singular.

The present disclosure relates to a surgical instrument for use with a surgical fastening apparatus or any other suitable surgical device. In fact, the presently disclosed surgical instrument can be applied to a whole line of surgical devices where torque is transmitted from one point to another. In addition, this surgical instrument can be employed in many kinds of surgical procedures. Surgeons may utilize the instrument in endoluminal procedures. During such procedures, surgeons introduce a surgical instrument through a body lumen. Doctors can also use the presently disclosed surgical instrument in endoscopic procedures. In this kind of procedure, doctors use a surgical instrument through or in combination with an endoscope.

Referring now to FIG. 1, a surgical instrument for use with a surgical fastening apparatus is generally designated as 100. In the interest of brevity, this disclosure will focus primarily on systems, methods and structures of surgical instrument 100. A detailed discussion of the remaining components and method of use of a surgical fastening apparatus is disclosed in U.S. Pat. No. 6,241,139, the entire content of which is incorporated herein by reference. Briefly, a surgical fastening apparatus comprising surgical instrument 100 includes an actuation apparatus 10. Surgical instrument 100 is releasably secured to a distal end of actuation apparatus 10.

Actuation apparatus 10 includes a motor 12, a gearshift lever 16, and gears 18. Motor 12 supplies input rotation to apparatus 10 and is operatively connected to at least one gear 18. Gears 18 are axially trapped between two columns 20 and are configured to mesh with each other. Each column has a pair of bores 21 extending therethrough. Bores 21 are configured to receive drive members 22. Drive members 22 are operatively coupled to flexible shafts 139. Gearshift lever 16 controls the axial movement of flexible shafts 139. A user can actuate gearshift lever 16 to translate flexible shafts 139 distally or proximally.

Additionally, apparatus 10 includes an articulation mechanism 30 including an articulation knob 32 and at least one steering wire 34. Articulation knob 32 is operatively coupled to at least one steering wire 34. In embodiment illustrated in FIG. 1, articulation knob 32 is operatively connected to two steering wires 34. A user can axially move steering wires 34 back and forth by rotating articulation knob 32. This axial motion causes the articulation of surgical instrument 100.

During operation, a user articulates surgical instrument 100 by pulling one steering wire 139. The movement of the steering wire bends gooseneck 130 and effectively articulates surgical instrument 100 to one side or the other. Gooseneck 130 bends towards the side of the wire that was pulled. In practice, the operator rotates articulation knob 32 apparatus 10 to move a steering wire 34 and thereby articulate surgical instrument 100.

Figure 2:
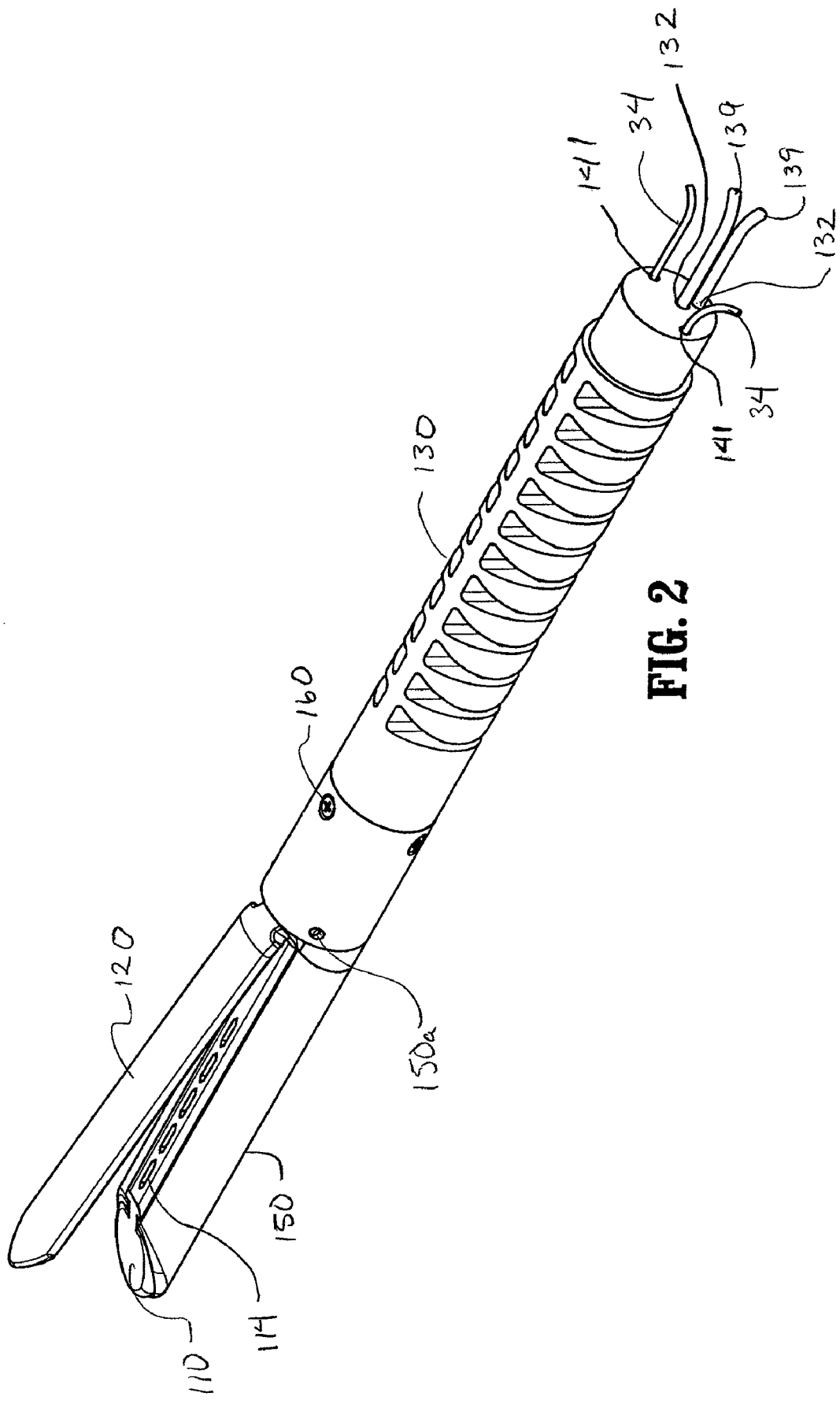
FIG. 2 is a perspective view of the surgical instrument of FIG. 1.

Referring to FIG. 2, surgical instrument 100 includes a gooseneck 130, channel 150, a cartridge 110, and an anvil 120 movably secured in relation to cartridge 110. Channel 150 partially encompasses cartridge 110. Cartridge 110, which can be replaceable, houses a plurality of fasteners 190 (see FIG. 3) in retention slots 114. Retention slots 114 can be arranged in a single row, as shown in FIG. 2, or in a plurality of rows. Gooseneck 130 is secured to channel 150. Specifically, a distal end of gooseneck 130 can be attached to a proximal end of channel 150. In turn, a proximal end of gooseneck 130 is operatively secured to the distal end of actuation apparatus 10. (See FIG. 1). Gooseneck 130 facilitates articulation of surgical instrument 100 and can be flexible.

Further, gooseneck 130 includes at least one hole 141 configured to receive a steering wire 34. The depicted embodiment shows a gooseneck 130 having two holes 141 extend therethrough. In addition, gooseneck 130 includes at least one bore 132 adapted to receive a flexible shaft 139. The illustrated embodiment shows a gooseneck 130 having two bores 132 extending through at least a portion of the length of gooseneck 130. Although the drawings show bores 132 having a cylindrical shape, bores 132 can have any suitable shape.

Flexible shafts 139 are operatively connected to each other and are configured to rotate in opposite directions, i.e., clockwise and counterclockwise. Since the flexible shafts 139 rotate in opposite directions, the torque transmitted by each flexible shaft 139 is canceled, thereby eliminating or substantially limiting the counter torque. As shown in FIG. 1, flexible shafts 139 are positioned on a neutral axis that extends along a portion of the length of surgical instrument 100. The depicted embodiment shows one flexible shaft 139 on top of the other. Flexible shafts 139, however, can be placed in numerous arrangements. For instance, flexible shafts 139 can consist of coaxial elongated members positioned on a neutral axis extending along at least a portion of the length of surgical instrument 100.

With reference to FIG. 3, gooseneck 130 surrounds at least a portion of flexible shafts 139 and steering wires 34. The distal end of gooseneck 130 is secured to the proximal end of channel 150 by a plurality of screws 160 positioned around the circumference of channel 150. Screws 160 are disposed in a plurality of threaded bores 144 disposed around the circumference of a transition member 140. Transition member 140 is internally interposed between gooseneck 130 and channel 150. Channel 150 has a plurality of holes 152 positioned around the circumference of its proximal end. Each hole 152 is designed to receive screws 160. Similarly, gooseneck 130 has a plurality of holes 136 configured to receive screws 160. Holes 136 of gooseneck 130 are located around the circumference of the distal end of gooseneck 130. Screws 160 attach gooseneck 130 to channel 150 through holes 152 of channel 150, holes 136 of gooseneck 130 and threaded bores 144 of transition member 140. To properly fix channel 150 to gooseneck 130, holes 152 of channel 150, threaded bores 144 of transition member 140, and holes 136 of gooseneck 130 are substantially aligned with each other.

Transition member 140 has at least one hole 143 disposed therethrough for receiving steering wires 34. Although FIG. 3 shows holes 143 having a cylindrical shape, it is envisioned that holes 143 can have any suitable shape. Additionally, transition member 140 includes at least one longitudinal hole 142 extending therethrough for receiving flexible shafts 139. In one embodiment, transition member 140 includes two holes 142 having a cylindrical shape. (See FIG. 3). Holes 142, however, can have any shape so long as they are adapted to receive flexible shafts 139.

A distal end of each flexible shaft 139 is operatively secured to a pinion shaft 138. Pinion shafts 138 are configured to rotate and, consequently, cause the rotation of pinions 154. Each pinion 154 is attached to a distal end of a pinion shaft 138. As seen in FIG. 26, pinions 154 include at least one tooth 154a or a plurality of teeth 154a. Tooth or teeth 154a extends radially as well as longitudinally. The longitudinal portion of tooth or teeth 154a is adapted to axially engage with gear couplers 156.

Returning to FIG. 3, each pinion 154 is configured to mesh with each other such that the rotation of a flexible shaft 139 rotates the other flexible shaft 139. As discussed hereinabove, a gear 18 is operatively attached to the proximal end of each flexible shaft 139. Gears 18 are configured to mesh with each other such that the rotation of one flexible shaft 139 rotates the other flexible shaft 139. Thus, flexible shafts 139 are operatively connected to each other at their proximal and distal ends. Since flexible shafts 139 are operatively connected with each other, one flexible shaft 139 is redundant. Only one flexible shaft 139 is needed to operate surgical instrument 100. If, for any reason, one flexible shaft 139 breaks, the other flexible shaft 139 can still actuate surgical instrument 100.

As shown in FIG. 26, the longitudinal portion of tooth or teeth 154a of each pinion 154 is adapted to axially engage with gear couplers 156. Gear couplers 156 have at least one longitudinal tooth or a plurality of teeth 156a, and at least one radial tooth or a plurality of teeth 156b. Longitudinal tooth or teeth 156a of gear couplers 156 extend proximally and are configured to axially engage with tooth or teeth 154a of pinions 154.

Returning to FIG. 3, clamp pinions 162 have at least one radial tooth or teeth 162a for meshing with radial tooth or teeth 154 of pinions 154 and are permanently attached to the distal ends of short lead screws 158. The longitudinal length of short lead screws 158 is less than the longitudinal length of lead screws 112. Short lead screws 158 are axially trapped in transition member 140 and cartridge 110. Surgical instrument 100 can optionally include bearings to axially trap short lead screws 158.

In addition, surgical instrument 100 includes a link 122 positioned within a proximal end portion of channel 150. Particularly, a first end 122a of link 122 is pivotably connected to the proximal end of an anvil 120 by a link pin 126. A second end 122b of link 122 sits in a slot in cam clamp 164. Optionally, at least one projection 122c can extend from second end 122b of link 122. Projections 122c can pivotably fix link 122 to clamp cam 164.

Clamp cam 164 is positioned within an inner proximal portion of channel 150 and includes at least one bore 164a for receiving pinion shafts 138, at least one bore 164b for receiving at least one short lead screw 158, and a slot 164c configured to receive at least a portion of anvil 120, as seen in FIG. 4. At least a portion of each pinion shaft 138 is disposed in bores 164a. Short lead screws 158 are threadedly engaged to threaded bores 164b of cam clamp 164. The rotation of short lead screws 158 causes the translation of cam clamp 164 proximally or distally. During operation, as cam clamp 164 moves proximally, projections 122c slides along the inner diameter of channel 150, link 122 becomes more vertical, raising proximal end of anvil 120 and causing the distal end of anvil 120 to drop and clamp tissue. Conversely, the distal motion of cam clamp 164 causes projections 122c to slide distally within channel 150. As projections 122c move distally, the proximal end of anvil 120 descends, causing the distal end of anvil 120 to ascend and unclamp tissue.

Figure 5:
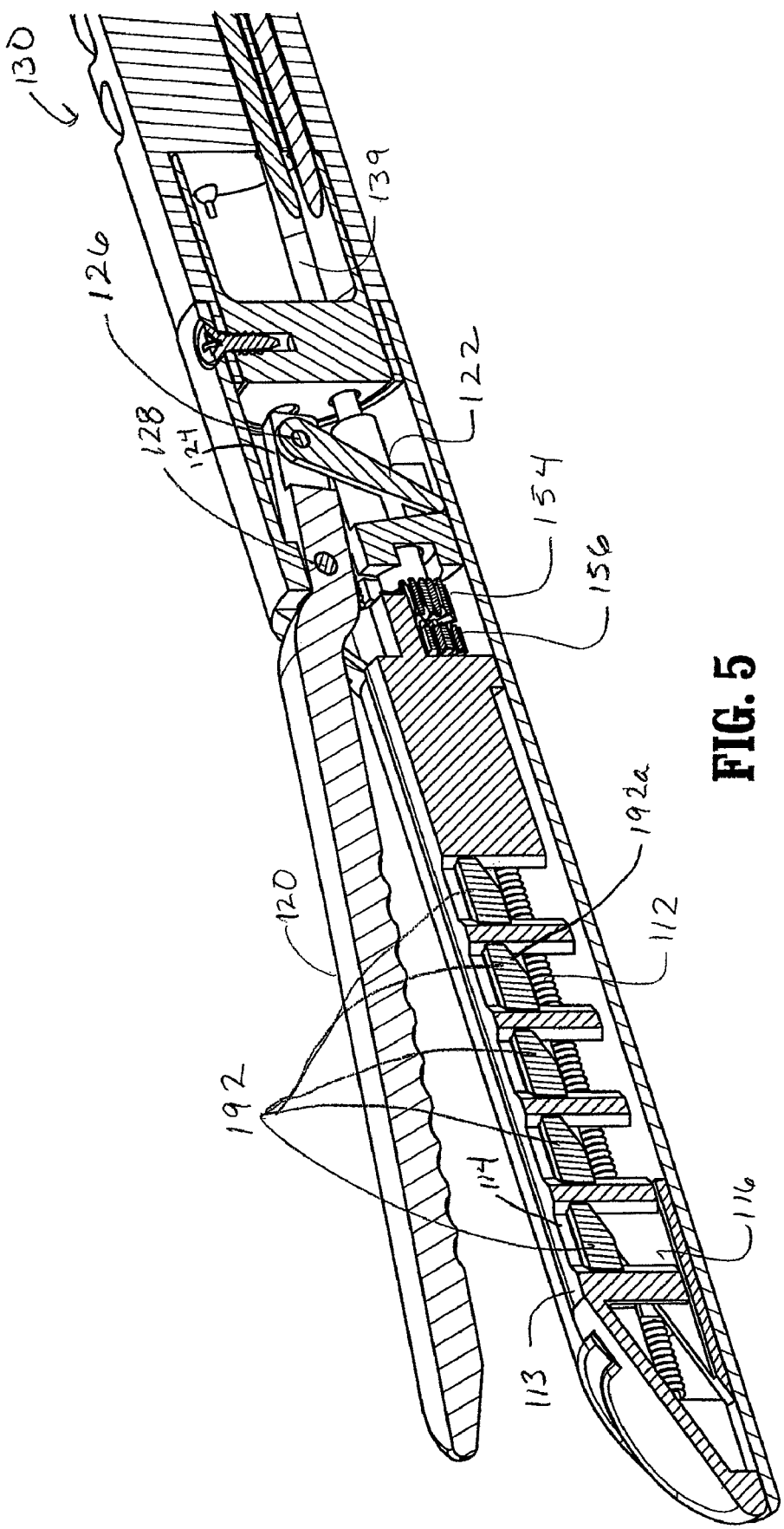
FIG. 5 is a perspective longitudinal cross-sectional view of the surgical instrument of FIGS. 1-3.
Figure 6:
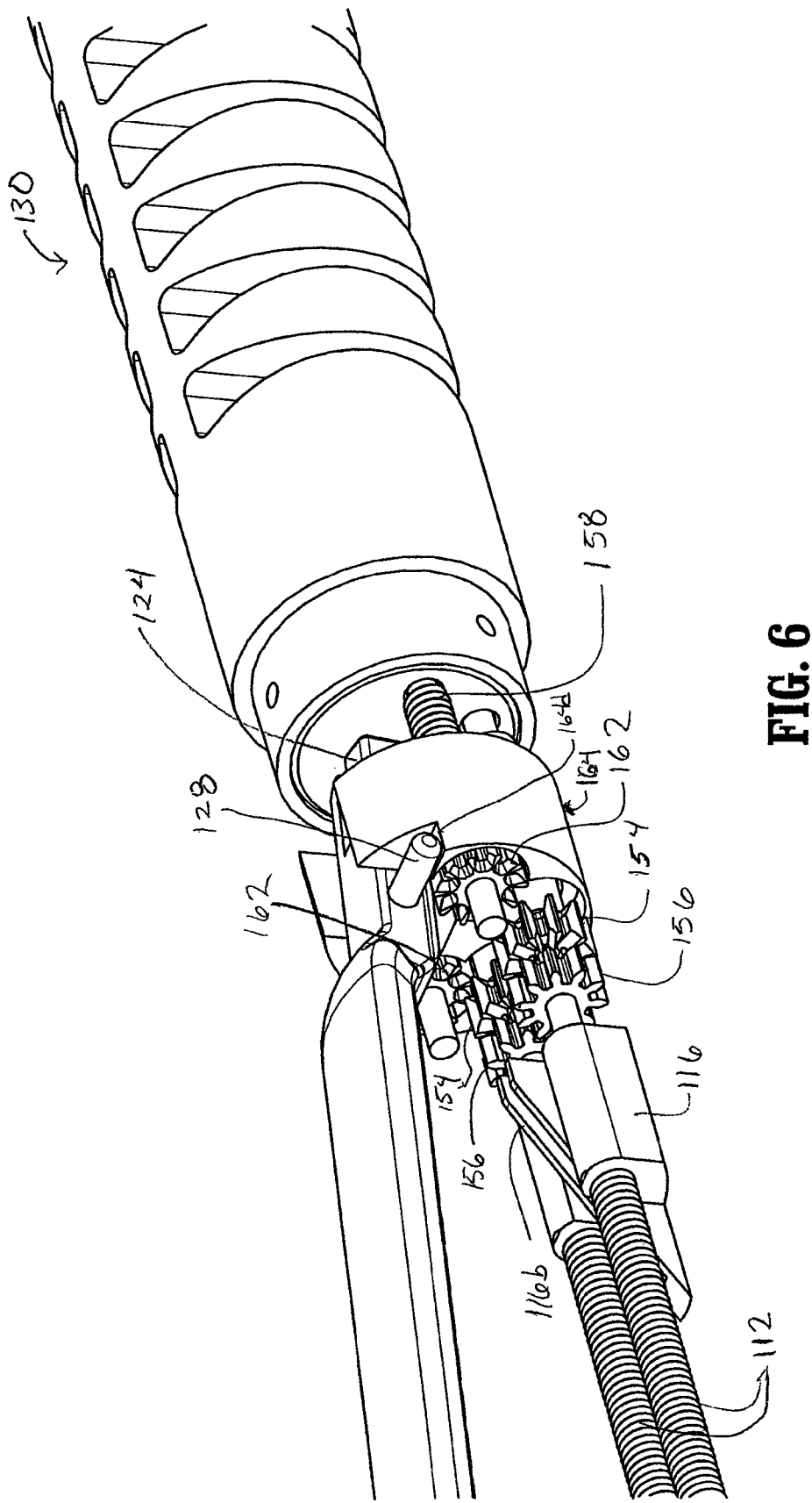
FIG. 6 is a perspective view of a portion of the surgical instrument of FIGS. 1-3.
Figure 7:
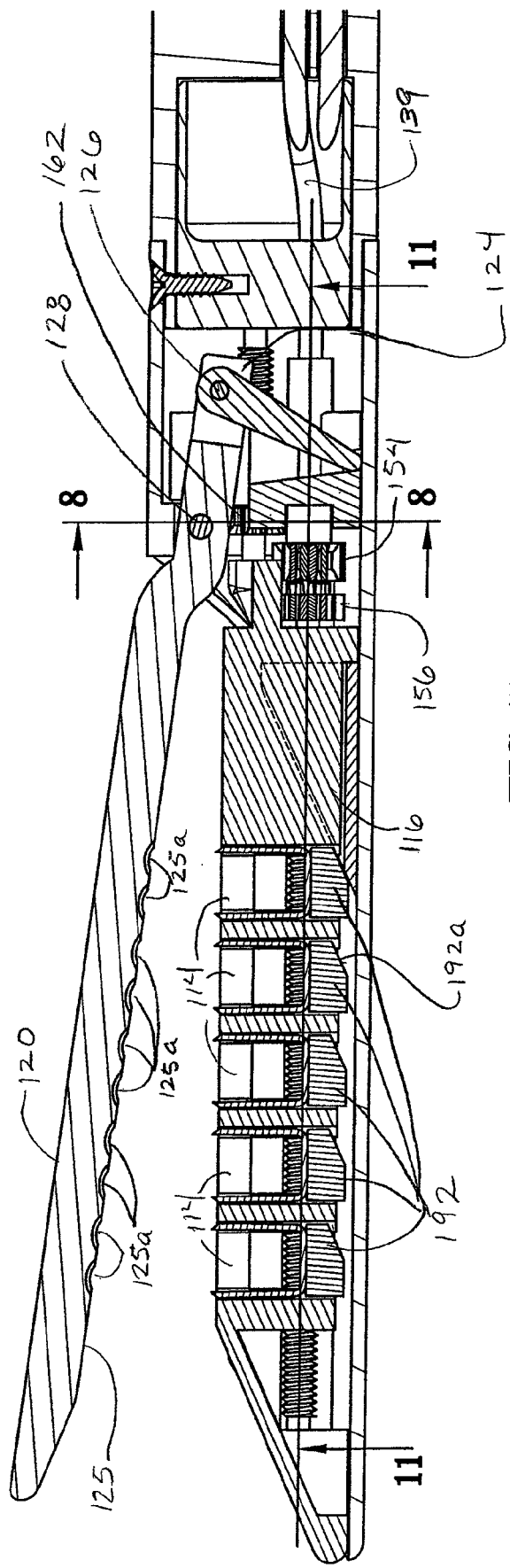
FIG. 7 is a side cross-sectional view of the surgical instrument of FIGS. 1-3.

With reference to FIG. 5-7, each gear coupler 156 is mounted to the proximal end of each lead screw 112. Lead screws 112 are at least partially threaded and are at least partially disposed within cartridge 110, as shown in FIG. 5. Cartridge 110 includes a tissue contacting surface 113 having at least one row of longitudinally spaced-apart retention slots 114, a plurality of pushers 192, a plurality of fasteners 190, and a sled 116 slidably positioned therein. Retention slots 114 are adapted to receive fasteners 190. Those skilled in the art will contemplate a cartridge 110 with any number of rows of retention slots 114. For example, cartridge 110 may include two rows of retention slots 114. In this embodiment, a knife can be placed between these two rows of retention slots 114. Nonetheless, irrespective of the number rows of retention slots 114, cartridge 110 can include a knife to cut tissue. The knife can be operatively attached to sled 116. Additionally, the cartridge may include an electrical or mechanical interlock mechanism to prevent distal motion of sled 116 unless anvil 120 is in its closed position.

Sled 116 includes a cam member 116b and at least one threaded bore 116a adapted to receive lead screw 112. Pushers 192 have a surface 192a that cooperates with and is complementary to cam member 116 of sled 116. During operation of surgical instrument 100, sled 116 translates through cartridge 110 to advance cam member 116b into sequential or simultaneous contact with pushers 192, to cause pushers 192 to translate vertically within retention slots 114 and urge fasteners 190 from retention slots 114 into the staple deforming concavities 125a of an anvil 120. The staple deforming cavities 120a are configured to crimp staples.

Anvil 120 includes a tissue contacting surface 125 having a plurality of staple deforming concavities 125a. A single staple deforming concavity 125a can be adapted to cooperate with the legs of one fastener 190. Alternatively, two or more staple deforming concavities 125a can cooperate with the legs of a single fastener 190.

A pivot pin 128 pivotably secures anvil 120 to channel 150. Channel 150 has at least one hole 150a designed to receive pivot pin 128, as seen in FIG. 2. Pivot pin 180 rests on a support surface 164d of clamp cam 164, as shown in FIG. 6. A proximal end portion 124 of anvil 120 is positioned within channel 150. Link pin 126 pivotably attaches proximal end portion 124 of anvil 120 and link 122.

As discussed hereinabove, channel 150 encompasses at least a portion of cartridge 110. Optionally, screws 153 can connect channel 150 and cartridge 110 with each other, as seen in FIG. 3. In this embodiment, channel 150 includes at least one hole 151 configured to receive a screws 153.

Figure 8:
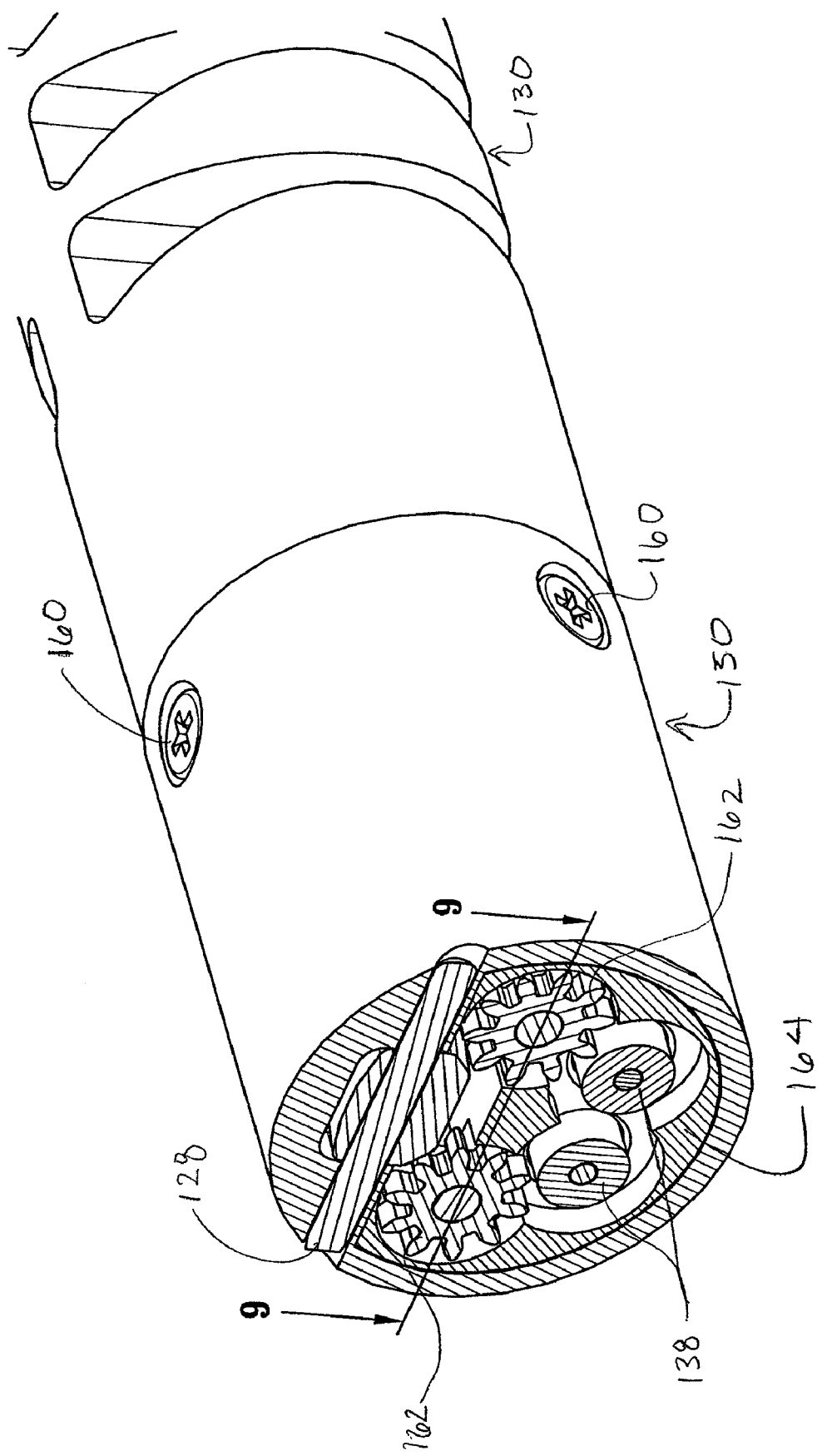
FIG. 8 is a perspective cross-sectional view of the surgical instrument of FIGS. 1-3, as taken through section lines 8-8 of FIG. 7.
Figure 11:
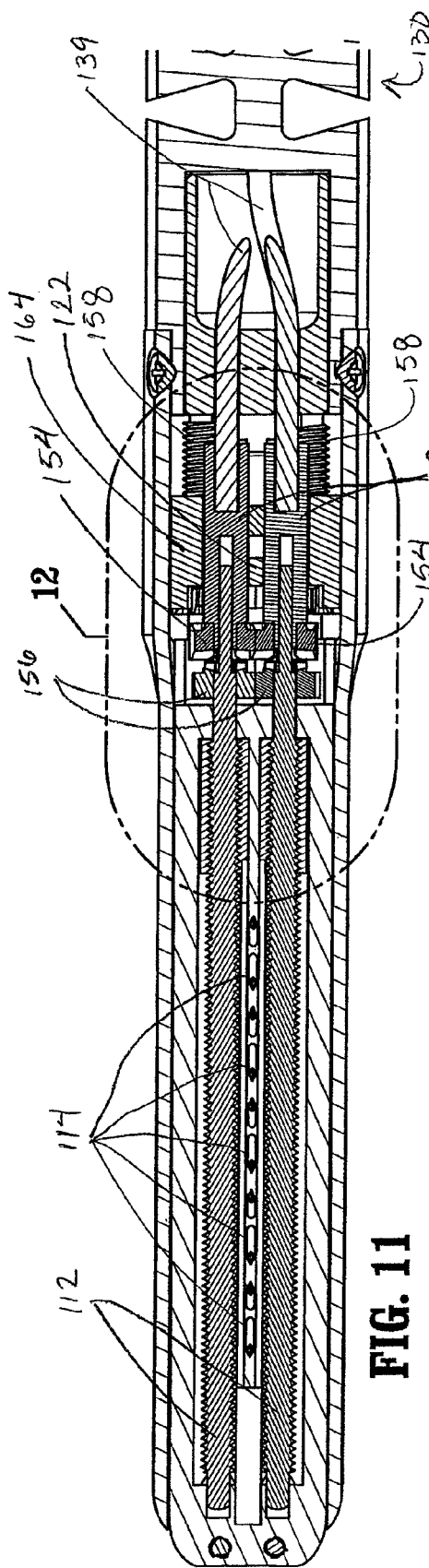
FIG. 11 is a top cross-sectional view of the surgical instrument of FIGS. 1-3, as taken through section lines 11-11 of FIG. 7.
Figure 12:
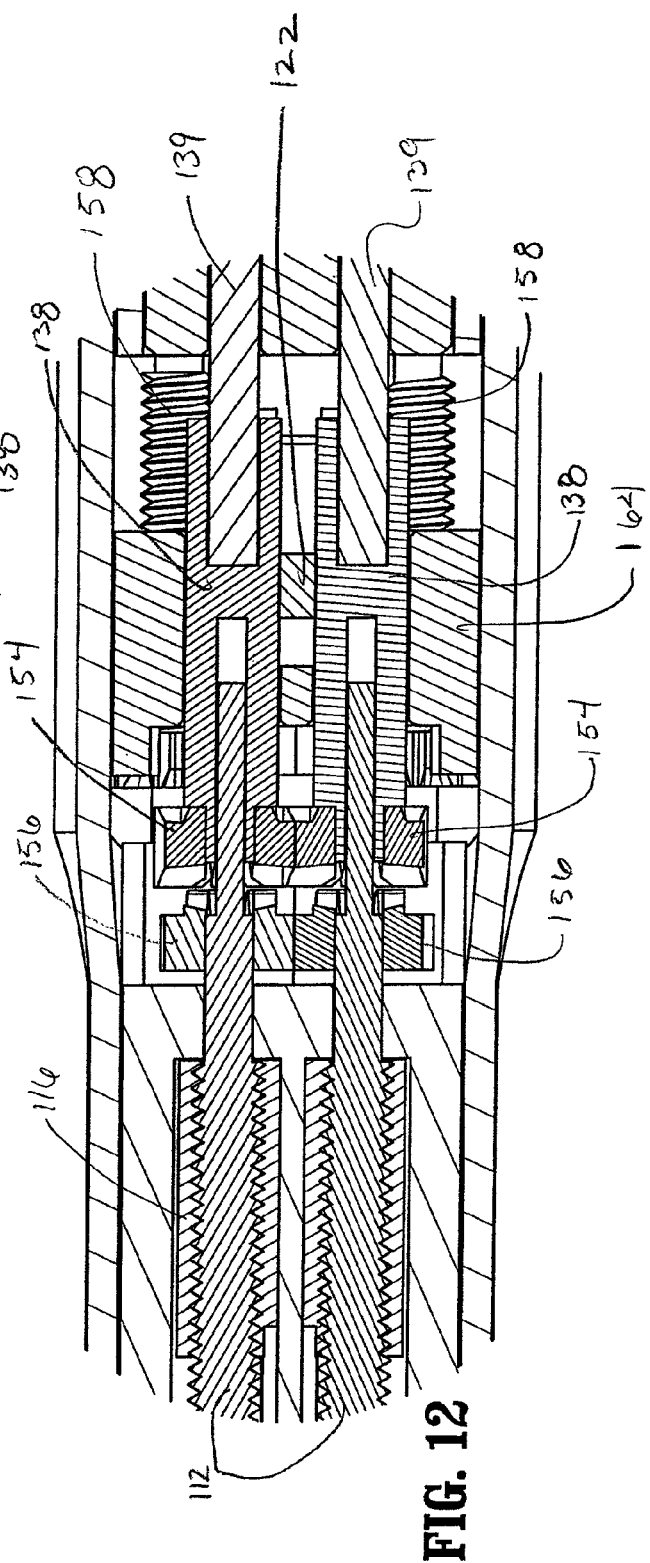
FIG. 12 is a top sectional view of the surgical instrument of FIGS. 1-3, as taken around section 12 of FIG. 11.

In operation, surgical instrument 100 applies fasteners 190 to tissue whilst, at the same time, eliminating or substantially limiting counter torque. During use, an operator must first make sure that the surgical instrument 100 is in its neutral position, as shown in FIGS. 7 and 8. When surgical instrument 100 is in its neutral position, anvil 120 and cartridge 110 are spaced apart from each other and pinions 154 are not meshed with clamp pinions 162, as seen in FIGS. 7-10. Additionally, in the neutral position, sled 116 is disposed on a proximal portion of cartridge 110 (see FIG. 7) and pinions 154 are not axially engaged with gear couplers 156 (see FIGS. 11 and 12). It is also contemplated that the surgical instrument could be configured to eliminate the neutral position and simply operate in a sequential closure-fire-open mode.

After placing surgical instrument 100 in its neutral position, a user may approximate it to a tissue portion. To position surgical instrument 100 in the desired surgical site, an operator can endoluminally introduce surgical instrument 100 into the body through a body lumen. Alternatively, an operator can use surgical instrument 100 through or in combination with an endoscope to reach the desire location. The tissue portion should be located between anvil 120 and cartridge 110.

Figure 13:
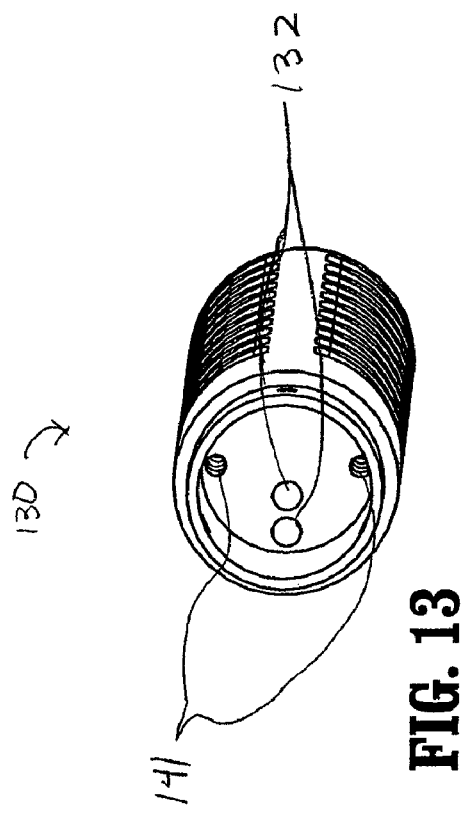
FIG. 13 is a perspective view of the gooseneck of a surgical instrument in accordance with an embodiment of the present disclosure.
Figure 14:
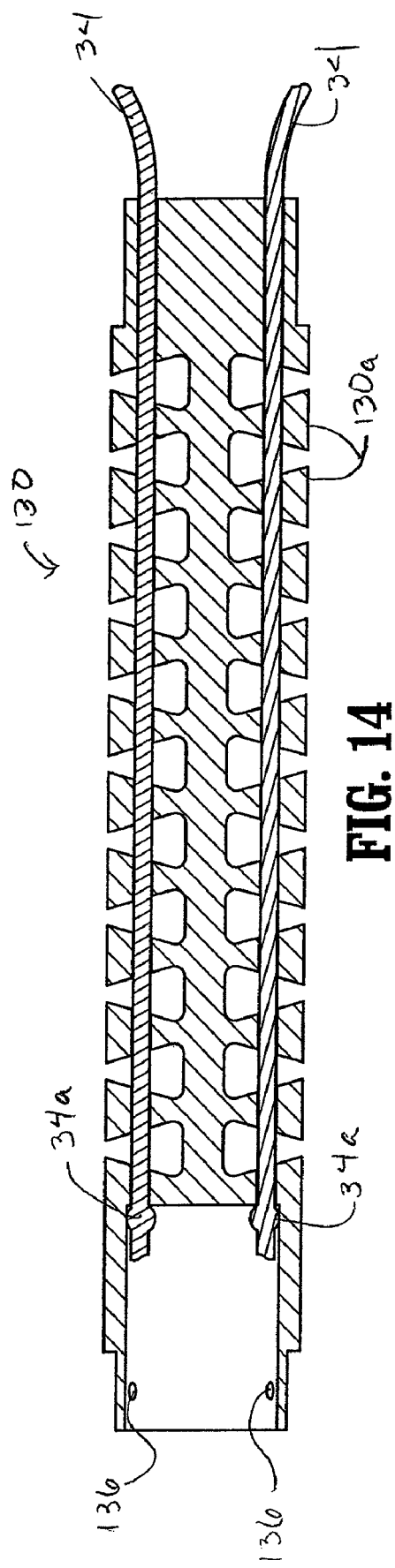
FIG. 14 is a top cross-sectional view of the gooseneck of a surgical instrument in accordance with an embodiment of the present disclosure.

A user can articulate surgical instrument 100 to position it on the desired location by moving steering wires 34. As discussed hereinabove, an embodiment of the presently disclosed surgical instrument 100 includes a gooseneck 130 having two holes 141 each adapted to receive a steering wire 34, as seen in FIG. 13. As seen in FIG. 14, gooseneck 130 is at least partially formed by a plurality of triangular shaped sections 130a that are spaced apart from each other. In addition, gooseneck 130 is made of a flexible material. Each steering wire 34 includes a knot 34a to secure gooseneck 130 and steering wires 34 at their respective distal ends.

In use, an operator can rotate articulation knob 32 counterclockwise, as indicated by arrow "CCW," to translate proximally a steering wire 34, as indicated by arrow "A." In response to the proximal motion of steering wire 34, surgical instrument 100 articulates in the direction indicated by arrow "B." A user can also articulate surgical instrument 100 in the opposite direction by rotating articulation knob 32 clockwise.

Figure 19:
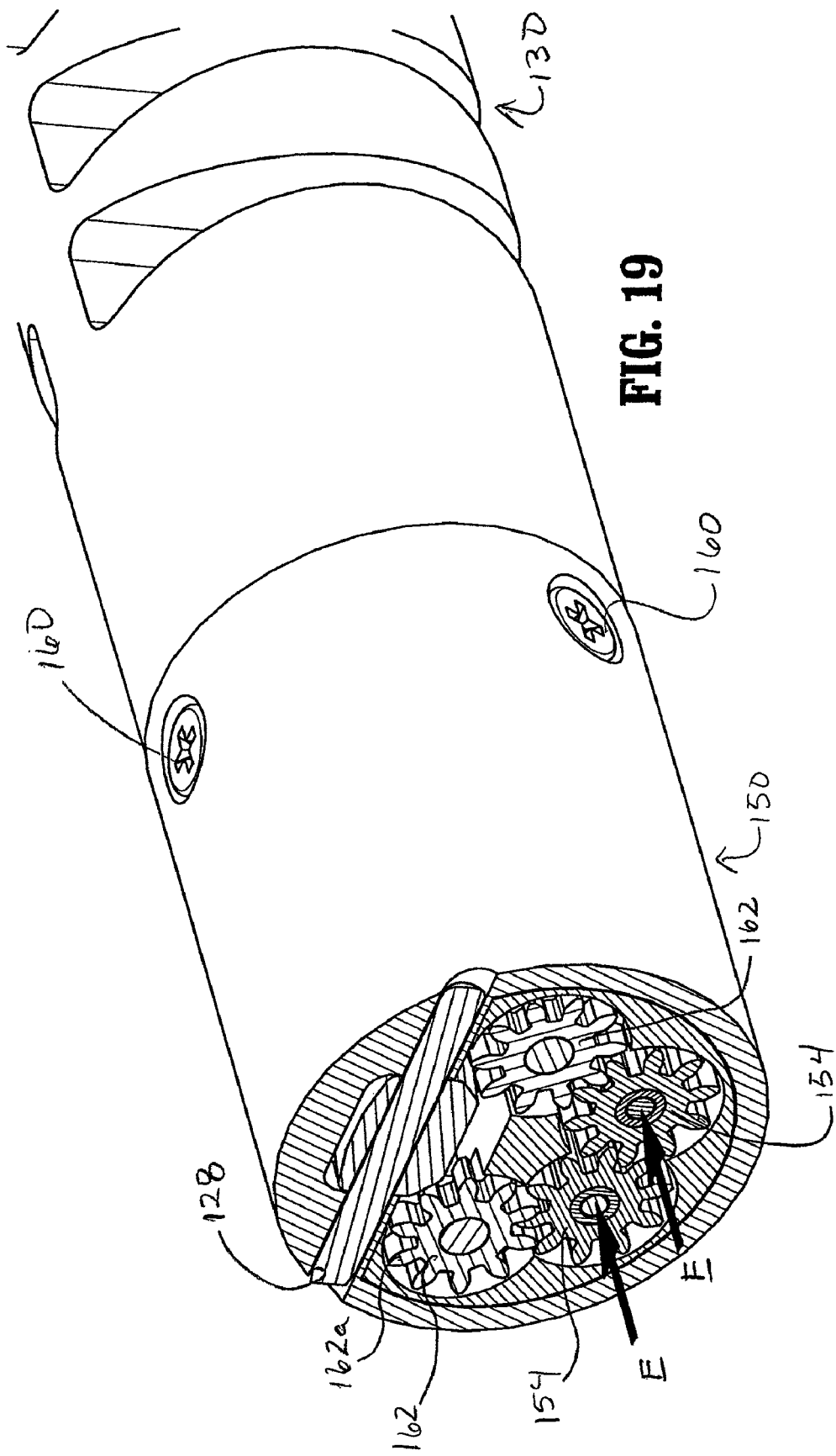
FIG. 19 is a perspective cross-sectional view of a portion of the surgical instrument of FIGS. 1-3, as taken through section lines 19-19 of FIG. 18.

Once the user places surgical instrument 100 in the desire surgical site, the user may move gearshift lever 16 proximally, as indicated by arrow "C," to translate flexible shafts 139 proximally in the direction indicated by arrows "D," as seen in FIGS. 17 and 18. The proximal motion of flexible shafts 139 consequently moves pinion 154 in the direction indicated by arrows "E" into a proximal position, as shown in FIGS. 18 and 19. When pinions 154 are located on the proximal position, radial teeth 154a of pinions 154 mesh with teeth 162a of clamp pinions 162, as shown in FIG. 19.

Figure 20:
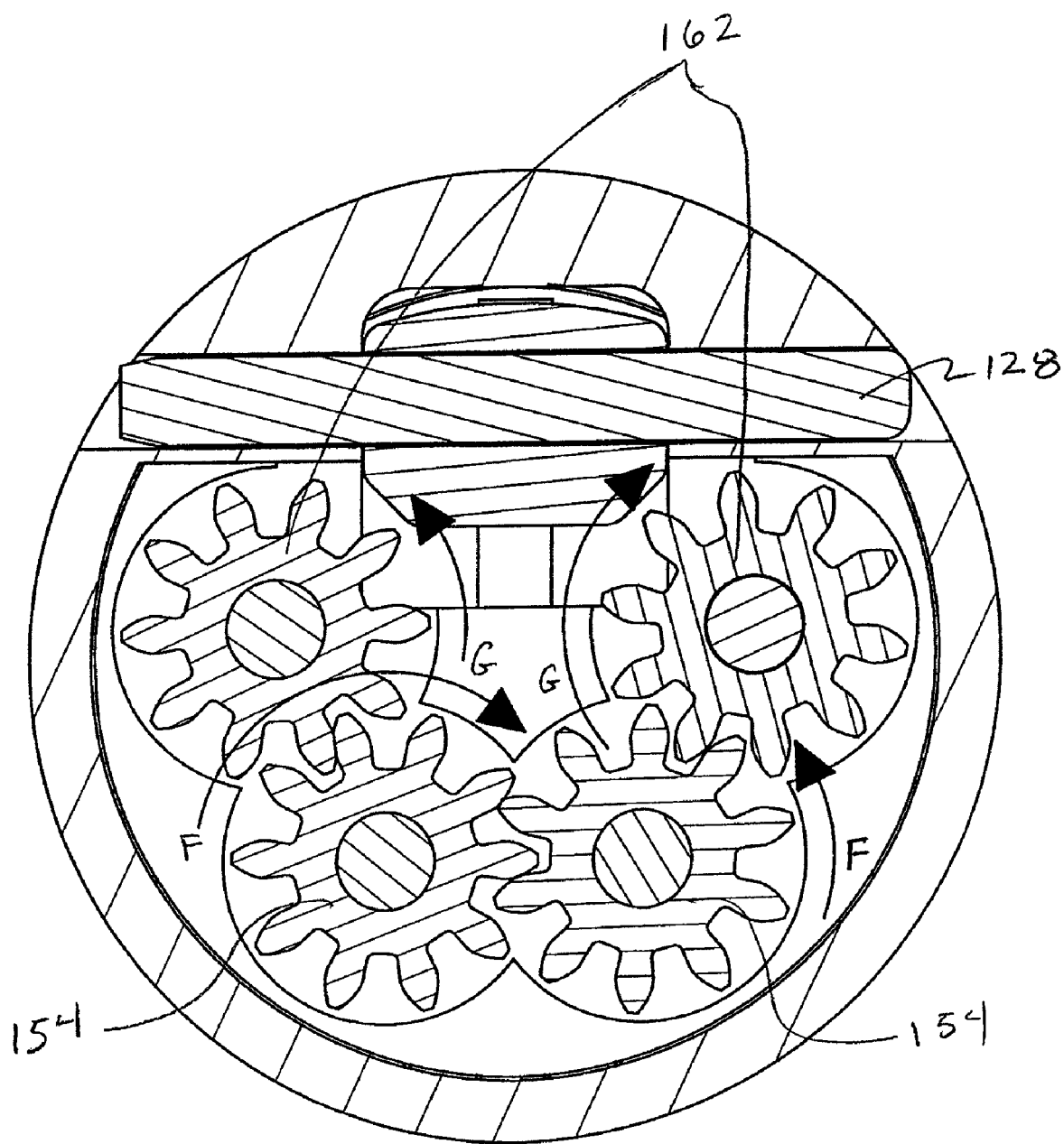
FIG. 20 is a front elevational view of the portion of the surgical instrument of FIG. 19.

After pinions 154 are placed in their proximal positions, a user can activate actuation apparatus 10 to rotate at least one flexible shaft 139. In one embodiment, actuation apparatus 10 rotates one flexible shaft 139 clockwise and the other flexible shaft 139 counterclockwise. The rotation of flexible shafts 139 in opposite directions eliminates or substantially reduces counter torque in surgical instrument 100. While flexible shafts 139 rotate, pinions 154 rotate in the direction indicated by arrows "F", as seen in FIG. 20. Since at this point radial teeth 154a of pinions 154 are meshed with teeth 162a of clamp pinions 162, as soon as pinions 154 rotate, clamp pinions 162 begin to rotate in the direction indicated by arrows "G," as illustrated in FIG. 20.

Figure 23:
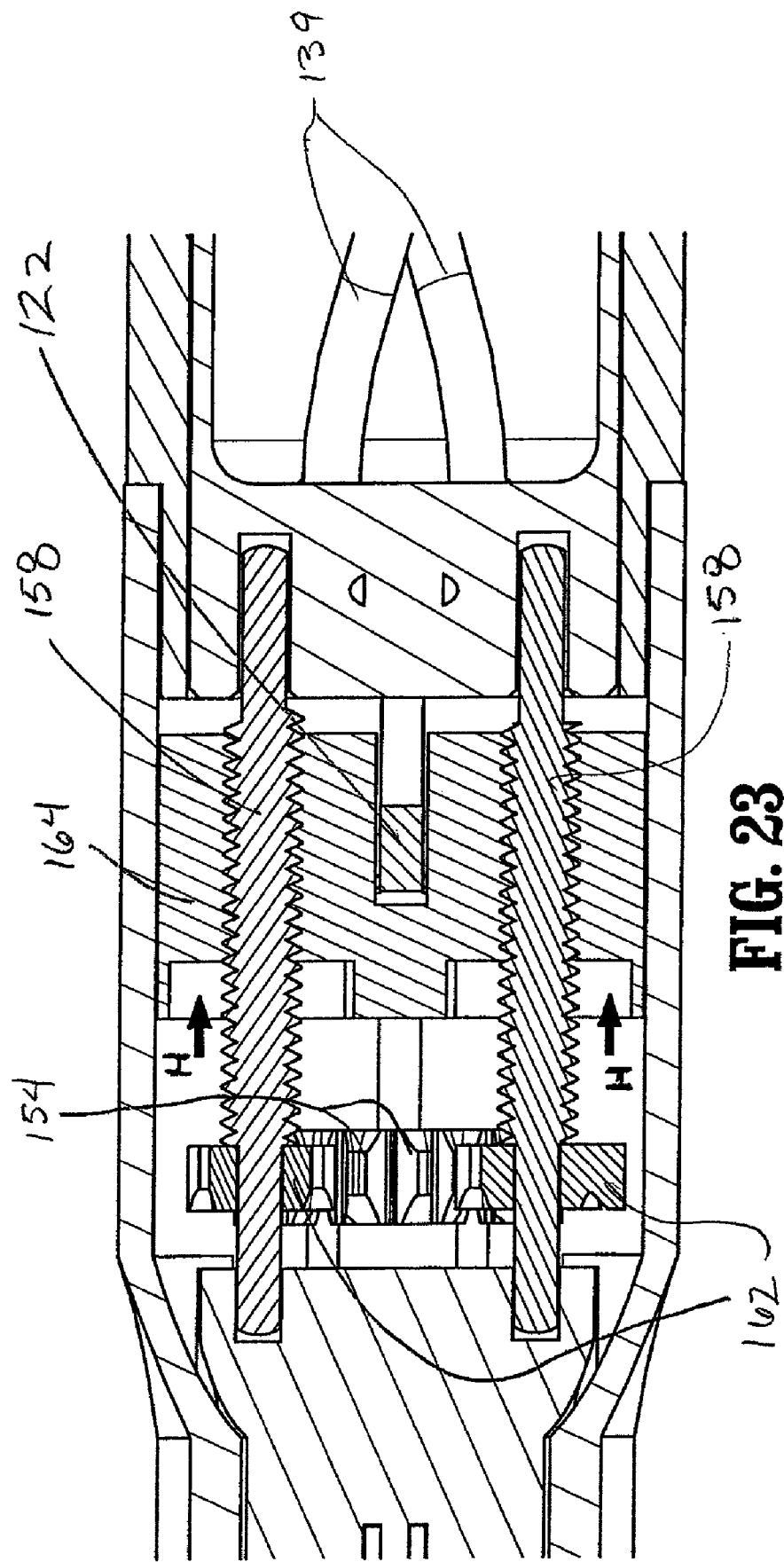
FIG. 23 is a top cross-sectional view of a portion of the surgical instrument of FIGS. 1-3.

With reference to FIGS. 21-23, when clamp pinions 162 rotate, cam clamp 164 translates proximally in the direction indicated by arrow "H." As cam clamp 164 moves proximally, link 122 pivots in a counterclockwise direction "I" with respect to pivot pin 126, raising proximal end of anvil 120. While the proximal end of anvil 120 moves vertically, the distal end of anvil 120 descends in the direction indicated by arrow "J" and clamps tissue.

Figure 27:
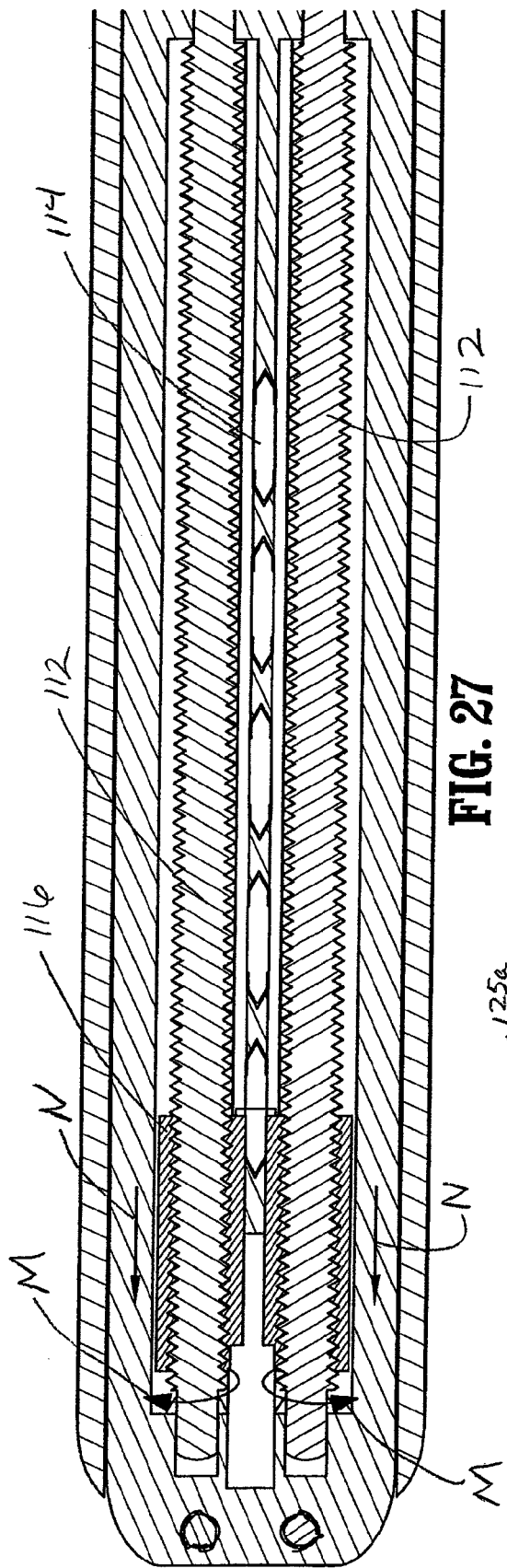
FIG. 27 is a top cross-sectional view of a portion of the surgical instrument of FIGS. 1-3.
Figure 28:
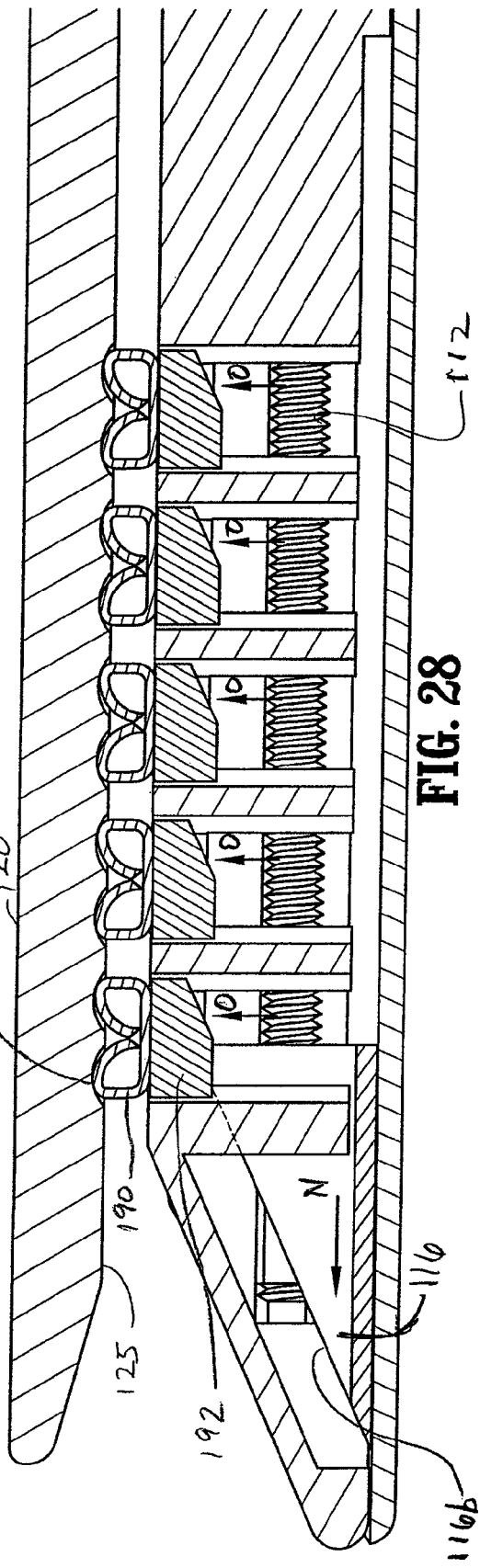
FIG. 28 is a side cross-sectional view of a portion of the surgical instrument of FIGS. 1-3.

With reference to FIG. 24-28, after clamping tissue, the operator can move gearshift lever 16, in the direction indicated by arrow "K," to translate flexible shafts 139 distally as indicated by arrow "L." When flexible shafts 139 are distally translated, teeth 154a of pinions 154 axially engage with longitudinal teeth 156a of gear couplers 156, as seen in FIG. 26. Once pinions 154 and gear couplers 156 are axially engaged with each other, gear couplers 156 rotates in response to the rotation of at least one flexible shaft 139. The rotation of gear couplers 156 causes the corresponding rotation of lead screws 112 in the direction indicated by arrows "M." While lead screws 112 rotate, sled 116 translates distally through cartridge 110 in the direction indicated by arrows "N," as depicted in FIG. 27. Sled 116 advances cam member 116b into sequential contact with pushers 192, to cause pushers 192 to translate vertically within retention slots 114 and eject fasteners 190. Pushers 192 displace fasteners 190 in the direction indicated by arrows "O" and towards the staple deforming concavities 125a of anvil 120, as shown in FIG. 28. An electrical or mechanical interlocking mechanism may be provided to prevent firing unless anvil 120 is in the closed position.

After clamping and stapling a tissue portion, the user can reverse the input rotation using apparatus 10. At this moment, at least one flexible shaft 139 rotates and causes the rotation of pinions 154. When pinions 154 rotate, clamp pinions 162 begin to rotate. The reverse rotation of clamp pinions 162 causes the distal translation of clamp cam 164. As clamp cam 164 moves distally, projections 122c of link 122 translate distally within channel 150. When projections 122c move distally, the proximal end of anvil 120 descends, causing the distal end of anvil 120 to rise and unclamp the tissue portion, as shown in FIG. 7. The reversed input rotation can optionally rotate lead screws 112 and translate proximally sled 116 to its original retracted position.

It will be understood that various modifications can be made to the embodiments disclosed herein. For example, the surgical instrument may include staples, two-part fasteners or any other suitable fastening element. Further, the cartridge can have a more than one row of longitudinally spaced apart retention slots. Further still, the cartridge can have any suitable elongated member capable of translating the sled instead of lead screws. Therefore, the above description should not be construed as limiting, but merely as exemplifications of embodiments. Those skilled in the art will envision other modifications within the scope and spirit of the present disclosure.

What is claimed is:

1. A surgical instrument, comprising:
an end effector; and first and second elongate shafts rotatably connected to each other at an end portion thereof such that rotation of one of the first and second elongate shafts causes rotation of the other elongate shaft to actuate the end effector, and wherein the first and second elongate shafts are movable axially relative to the end effector between a first position and a second position.

2. The surgical instrument according to claim 1, further comprising a gearshift lever configured to move the first and second elongate shafts longitudinally between the first and second positions.

3. The surgical instrument according to claim 2, wherein the first and second elongate shafts each include a gear at a respective proximal portion thereof, the gears being configured to mesh with each other such that rotation of one of the first and second elongate shafts causes rotation of the other elongate shaft.

4. The surgical instrument according to claim 3, further comprising first and second pinions, each pinion being operatively coupled to a distal portion of respective elongate shaft, wherein the pinions are configured to mesh with each other providing rotatable connection between the first and second elongate shafts.

5. The surgical instrument according to claim 2, wherein the end effector includes an anvil and a cartridge, the cartridge having a plurality of fasteners.

6. The surgical instrument according to claim 5, wherein when the elongate shafts are moved to the first position, rotation of the first and second elongate shafts moves the anvil and the cartridge between spaced and approximated positions.

7. The surgical instrument according to claim 5, wherein when the elongate shafts are in the second position, rotation of the first and second elongate shafts causes the plurality of fasteners to be ejected from the cartridge and toward the anvil.

8. The surgical instrument according to claim 5, further comprising a clamp cam, wherein movement of the clamp cam along a longitudinal axis of the surgical instrument causes relative motion between the anvil and the cartridge, the anvil and the cartridge being movable between spaced apart and approximated positions.

9. The surgical instrument according to claim 8, further comprising first and second members each including a clamp pinion rotatably connected to each other, the clamp pinions being configured to engage the pinions operatively coupled to the elongate shafts, wherein the clamp cam is translatably mounted on the first and second members such that rotation of the clamp pinions moves the clamp cam along the first and second members.

10. The surgical instrument according to claim 9, wherein when the elongate shafts are in the first position the pinions engage the clamp pinions, whereby the rotation of the first and second elongate shafts causes rotation of the clamp pinions which in turn moves the clamp cam along the first and second members.

11. The surgical instrument according to claim 9, wherein the first and second members are a lead screw.

12. The surgical instrument according to claim 5, wherein the end effector further includes at least one drive member adapted to axially move a sled disposed in the cartridge, the sled being adapted to drive the fasteners through tissue and toward the anvil.

13. The surgical instrument according to claim 12, wherein the at least one drive member is a lead screw.

14. The surgical instrument according to claim 12, wherein the at least one drive member includes at least one gear coupler configured to engage the pinions operatively coupled to the respective elongate shaft.

15. The surgical instrument according to claim 14, wherein when the elongate shafts are in the second position, the pinions engage the at least one gear coupler, whereby rotation of the first and second elongate shafts rotates the at least one gear coupler which in turn moves the sled.

16. The surgical instrument according to claim 2, further comprising a flexible neck attached to a proximal end of the end effector.

17. The surgical instrument according to claim 16, further comprising an articulation knob and at least one steering wire, the articulation knob being operatively coupled to the at least one steering wire, the at least one steering wire being coupled to the flexible neck such that rotation of the knob articulates the flexible neck.

18. The surgical instrument according to claim 1, wherein rotation of one of the first and second elongate shafts causes rotation of the other elongate shaft in an opposite direction to actuate the end effector.

19. The surgical instrument according to claim 1, wherein the first and second elongate shafts are flexible.

* * * * *